United States Patent
Takeuchi et al.

(10) Patent No.: US 6,620,933 B2
(45) Date of Patent: Sep. 16, 2003

(54) AZOMETHINE YELLOW DYE COMPOUND

(75) Inventors: Kiyoshi Takeuchi, Kanagawa (JP); Shigeki Uehira, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/254,599

(22) Filed: Sep. 26, 2002

(65) Prior Publication Data

US 2003/0125556 A1 Jul. 3, 2003

(30) Foreign Application Priority Data

Sep. 26, 2001  (JP) ........................................ 2001-293279

(51) Int. Cl.$^7$ .................... C07D 237/20; C07D 249/14; C07C 233/08
(52) U.S. Cl. .................... 544/332; 546/309; 548/265.4; 548/558; 549/480; 554/45; 558/394; 558/416; 560/13; 562/47; 562/52; 564/82; 564/86; 564/99; 564/164; 564/165
(58) Field of Search ........................ 548/265.4; 544/332; 564/165, 164, 82, 86, 99

(56) References Cited

PUBLICATIONS

Murakami, et al.: "Preparation of (Alkaneimidoyl) lanthanides and Their Reactions with Carbonyl Compounds" Bull. Chem. Soc. Jpn., 69, pp. 25–30 (1996).
Fahr, et al.: Tetrahedron Letters No. 34, pp. 3291–3293, (1967).
Sidgwick Journal of the Chemical Society, pp. 1191–1199 (1929).

*Primary Examiner*—Robert W. Ramsuer
(74) *Attorney, Agent, or Firm*—Birch, Stewart, Kolasch & Birch, LLP

(57) ABSTRACT

A azomethine yellow dye compound of general formula (I):
General formula (I)

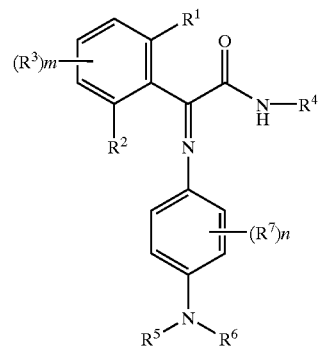

wherein $R^1$ and $R^2$ each independently represent a hydrogen atom or a substituent; $R^3$ represents a substituent; m indicates an integer from 0 to 3; when m is 2 or greater, $R^3$'s may be the same or different and may be mutually bonded to form a condensed ring; $R^3$ may be bonded to $R^1$ or $R^2$ to form a condensed ring; $R^4$ represents an aryl group or a heterocyclic group; $R^5$ and $R^6$ each independently represent a hydrogen atom or a substituent; $R^7$ represents a substituent; n indicates an integer from 0 to 4; when n is 2 or greater, $R^7$'s may be the same or different and the may be mutually bonded to form a condensed ring; $R^7$ may be bonded to $R^5$ or $R^6$ to form a condensed ring; and $R^5$ and $R^6$ may be bonded to each other to form a ring.

17 Claims, No Drawings

AZOMETHINE YELLOW DYE COMPOUND

BACKGROUND OF THE INVENTION

1. Field of the Invention

The present invention relates to an azomethine yellow dye compound having an aryl group bonded to a carbon atom in an azomethine moiety thereof, which is useful as yellow dye for silver halide photographic photosensitive materials, yellow dye for printing materials used in inkjet or thermal transfer printing or the like, yellow dye for toner in electrophotography, yellow dye for prints, yellow dye for color proofs, yellow dye for optical memory media, yellow dye for organic electroluminescence elements, filter dye for solid-state image pickup tubes or color liquid-crystal televisions, and also as an intermediate in the production thereof.

2. Description of the Related Art

Many types of yellow azomethine dyes are generally known and are used as yellow dye compounds used for silver halide photographic photosensitive materials and also as dyes or colorants for other various purposes. Especially for silver halide photographic photosensitive materials, azomethine dyes having an aniline derivative bonded to the nitrogen atom in an azomethine moiety thereof and having an acyl group, a carbamoyl group, an alkoxycarbonyl group or the like bonded to a carbon atom in said moiety are widely known. These dyes can be formed by reacting an active methylene compound (generally a yellow coupler) provided in a silver halide photographic photosensitive material with an oxide product of a p-phenylenediamine based developing agent when the photographic photosensitive material is developed, and these dyes have been used as photographic dye.

However, these yellow azomethine dyes are problematic in that an absorption coefficient thereof is small and a hydrolysis stability thereof against acid is low. As one means for solving these problems, use of azomethine yellow dye compounds having an aryl group and a carbamoyl group both bonded to a carbon atom in an azomethine moiety thereof has been taken into consideration. Some azomethine compounds having an aryl group and a carbamoyl group both bonded to a carbon atom in an azomethine moiety thereof are described in, for example, *Farmaco*, 54, 39 (1999); *Pestic. Sci.*, 44, 49 (1995); *J. Pract. Chem.*, 128, 1 (1930), *Zh. Obshch. Khim.*, 26, 1169 (1956); and *Zh. Obshch. Khim.*, 26, 2019 (1956). In all of these azomethine dye compounds described therein, however, a nitrogen atom in the carbamoyl group bonded to the carbon atom in the azomethine moiety is bonded to the aryl group that is bonded to the carbon atom in the azomethine moiety either directly or via a linking group, such as carbonyl group, provided therebetween. Further, these dye compounds are still problematic in that a color hue thereof is not good. These azomethine dye compounds described above are not those of a type having a hydrogen atom bonded to the nitrogen atom in the carbamoyl group therein.

On the other hand, some other azomethine compounds having an aryl group and a carbamoyl group, which has a hydrogen atom bonded to a nitrogen atom thereof, with both groups being bonded to a carbon atom in the azomethine moiety thereof, as described, for example, in *J. Org. Chem. USSR*, 10, 609 (1974); *J. Pract. Chem.*, 114, 332; *Tetrahedron Lett.*, 1967, 3291; *Justus Liebigs Ann. Chem.*, 442, 266 (1926); *J. Pract. Chem.*, 114, 332 (1926); *J. Chem. Soc.*, 1929, 1198; and *Bull. Chem. Soc. Jpn.*, 69, 25 (1996), are known. However, these compounds do not have an amino group at a para-position of a phenyl group bonded to the nitrogen atom in the azomethine moiety thereof, and furthermore, since a maximum absorption wavelength thereof is short, they con not be used as yellow dye.

As described above, an azomethine yellow dye having a p-aminophenyl group bonded to the nitrogen atom in an azomethine moiety thereof, and having an aryl group and a carbamoyl group both bonded to a carbon atom in the azomethine moiety thereof with the carbamoyl group having a hydrogen atom bonded to a nitrogen atom in the carbamoyl group, is completely unknown.

SUMMARY OF THE INVENTION

An object of the present invention is to provide an azomethine yellow dye compound that has a large absorption absorption coefficient and is stable against acid hydrolysis. The dye compound has a p-aminophenyl group bonded to a nitrogen atom in an azomethine moiety thereof and has an aryl group and a carbamoyl group both bonded to a carbon atom in the azomethine moiety thereof. The carbamoyl group has a hydrogen atom bonded to a nitrogen atom thereof.

Having assiduously studied the problems noted above, the present inventors have found that these problems can be solved by the following method.

A first aspect of the present invention is an azomethine yellow dye compound represented by the following general formula (I).

General formula (I)

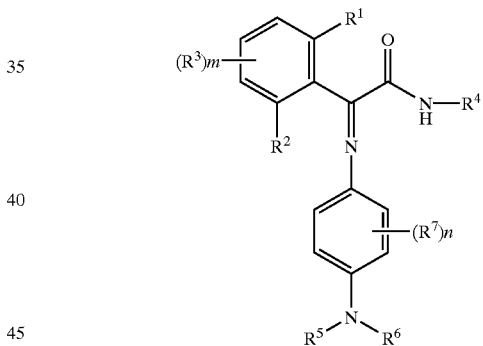

In the general formula (I), $R^1$ and $R^2$ each independently represent a hydrogen atom or a substituent; $R^3$ represents a substituent; m indicates an integer from 0 to 3; when m is 2 or greater, $R^3$'s may be the same as or different from each other, and the $R^3$'s may be bonded to each other to form a condensed ring; $R^3$'s may be bonded to $R^1$ or $R^2$ to form a condensed ring; $R^4$ represents an aryl group or a heterocyclic group; $R^5$ and $R^6$ each independently represent a hydrogen atom or a substituent; $R^7$ represents a substituent; n indicates an integer from 0 to 4; and when n is 2 or greater, $R^7$'s may be the same as or different from each other, and the $R^7$'s may be bonded to each other to form a condensed ring; $R^7$ may be bonded to $R^5$ or $R^6$ to form a condensed ring; and $R^5$ and $R^6$ may be bonded to each other to form a ring.

DESCRIPTION OF THE PREFERRED EMBODIMENTS

The compound of the present invention, which is represented by the following general formula (I), is described in detail below.

General formula (I)

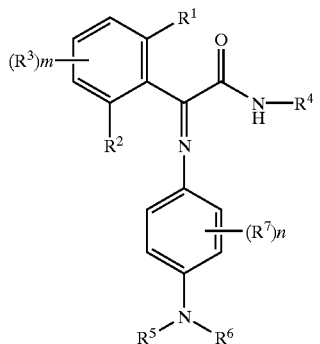

In the formula (I), $R^1$ and $R^2$ each independently represent a hydrogen atom or a substituent; $R^3$ represents a substituent; m indicates an integer from 0 to 3; and when m is 2 or greater, $R^3$'s may be the same as or different from each other, and the $R^3$'s may be bonded to each other to form a condensed ring; $R^3$ may be bonded to $R^1$ or $R^2$ to form a condensed ring; $R^4$ represents an aryl group or a heterocyclic group; $R^5$ and $R^6$ each independently represent a hydrogen atom or a substituent; $R^7$ represents a substituent; n indicates an integer from 0 to 4; when n is 2 or greater, $R^7$'s may be the same as or different from each other, and the $R^7$'s may be bonded to each other to form a condensed ring; $R^7$ may be bonded to $R^5$ or $R^6$ to form a condensed ring; and $R^5$ and $R^6$ may be bonded to each other to form a ring. Herein, "substituent" means a substituting group other than a hydrogen atom.

In general formula (I), $R^1$ and $R^2$ each independently represent a hydrogen atom or a substituent. Examples of the substituent include ahalogen atom, an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic-oxy group, an acyloxy group, a carbamoyloxy group, an alkoxycarbonyloxy group, an aryloxycarbonyloxy group, an amino group (examples of which include an alkylamino group, an arylamino group and a heterocyclic amino group), an acylamino group, an aminocarbonylamino group, an alkoxycarbonylamino group, an aryloxycarbonylamino group, a sulfamoylamino group, an alkylsulfonylamino group, arylsulfonylamino group, a mercapto group, an alkylthio group, an arylthio group, a heterocyclic-thio group, a sulfamoyl group, a sulfo group, an alkylsulfinyl group, arylsulfinyl group, an alkylsulfonyl group, arylsulfonyl group, an aryloxysulfinyl group, an alkoxysulfinyl group, an aryloxysulfonyl group, an alkoxysulfonyl group, an acyl group, an aryloxycarbonyl group, an alkoxycarbonyl group, a carbamoyl group, an aryl or heterocyclic-azo group, an imido group, a phosphino group, a phosphinyl group, a phosphinyloxy group, a phosphinylamino group, and a silyl group.

The substituents for $R^1$, $R^2$, $R^3$, $R^4$, $R^5$, $R^6$ and $R^7$ may be further substituted, for example, with any of those groups mentioned above.

More particularly, examples of the substituent for $R^1$ and $R^2$ include halogen atoms (e.g., chlorine, bromine and iodine), an alkyl group (the alkyl group may be a linear or branched, substituted or unsubstituted alkyl group, and the group preferably has from 1 to 30 carbon atoms, e.g., methyl, ethyl, n-propyl, isopropyl, t-butyl, n-octyl, eicosyl, 2-chloroethyl, 2-cyanoethyl and 2-ethylhexyl), a cycloalkyl group [this cycloalkyl group is preferably a substituted or unsubstituted cycloalkyl group having from 3 to 30 carbon atoms, e.g., cyclohexyl, cyclopentyl, 4-n-dodecylcyclohexyl and a polycycloalkyl group having a polycyclic structure, examples of the polycycloalkyl group including a bicycloalkyl group (the bicycloalkyl group is preferably an unsubstituted or substituted group having from 5 to 30 carbon atoms, such as bicyclo[1,2,2]heptan-2-yl or bicyclo[2,2,2]octan-3-yl) and a tricycloalkyl group, and the cycloalkyl group is preferably a monocyclic cycloalkyl group or a bicycloalkyl group, and more preferably a monocyclic cycloalkyl group], an alkenyl group (examples of the alkenyl group include a linear or branded, substituted or unsubstituted alkenyl group preferably having from 2 to 30 carbon atoms, e.g., vinyl, allyl, prenyl, geranyl and oleyl), a cycloalkenyl group [examples of this cycloalkenyl group include substituted or unsubstituted cycloalkenyl groups preferably having from 3 to 30 carbon atoms, e.g., 2-cyclopenten-1-yl and 2-cyclohexen-1-yl, and includes a polycycloalkenyl group having a polycyclic structure, such as, a tricycloalkenyl group and a bicycloalkenyl group (examples of the bicycloalkenyl group include unsubstituted or substituted bicycloalkenyl group, preferably having from 5 to 30 carbon atoms, e.g., bicyclo[2,2,1]hept-2-en-1-yl and bicyclo[2,2,2]oct-2-en-4-yl), and the cycloalkenyl group is preferably a monocyclic cycloalkenyl group or a bicycloalkenyl group, and more preferably a monocyclic cycloalkenyl group], an alkynyl group (examples of the alkynyl group include substituted or unsubstituted alkynyl groups preferably having from 2 to 30 carbon atoms, e.g., ethynyl, propargyl and trimethylsilylethynyl), an aryl group (examples of the aryl group include substituted or unsubstituted aryl groups, preferably having from 6 to 30 carbon atoms, e.g., phenyl, p-tolyl, naphthyl, m-chlorophenyl and o-hexadecanoylaminophenyl), a heterocyclic group (the heterocyclic group is preferably a monovalent group derived from a substituted or unsubstituted, aromatic or non-aromatic, heterocyclic compound, which has 5- or 6-members, by removing one hydrogen atom from the compound, and more preferably the heterocyclic group is a 5-membered or 6-membered aromatic heterocyclic group having from 3 to 30 carbon atoms, e.g., 2-furyl, 2-thienyl, 2-pyrimidinyl and 2-benzothiazolyl), a cyano group, a hydroxyl group, a nitro group, a carboxyl group, an alkoxy group (examples of the alkoxy group include substituted or unsubstituted alkoxy groups, preferably having from 1 to 30 carbon atoms, e.g., methoxy, ethoxy, isopropoxy, t-butoxy, n-octyloxy and 2-methoxyethoxy), an aryloxy group (examples of the aryloxy group include substituted or unsubstituted aryloxy groups, preferably having from 6 to 30 carbon atoms, e.g., phenoxy, 2-methylphenoxy, 4-t-butylphenoxy, 3-nitrophenoxy and 2-tetradecanoylaminophenoxy), a silyloxy group (the silyloxy group preferably has from 3 to 20 carbon atoms, e.g., trimethylsilyloxy and t-butyldimethylsilyloxy), a heterocyclic-oxy group (examples of the heterocyclic-oxy group include substituted or unsubstituted heterocyclic-oxy groups preferably having from 2 to 30 carbon atoms, e.g., 1-phenyltetrazol-5-oxy and 2-tetrahydropyranyloxy), an acyloxy group (preferable examples of the acyloxy group include a formyloxy group, a substituted or unsubstituted alkylcarbonyloxy group having from 2 to 30 carbon atoms, and a substituted or unsubstituted aryloxycarbonyl group having from 6 to 30 carbon atoms, e.g., formyloxy, acetyloxy, pivaloyloxy, stearoyloxy, benzoyloxy, and p-methoxyphenylcarbonyloxy), a carbamoyloxy group (examples of the carbamoyloxy group include substituted or unsubstituted carbamoyloxy groups preferably having from 1 to 30 carbon atoms, e.g., N,N-dimethylcarbamoyloxy, N,N-diethylcarbamoyloxy, morpholinocarbonyloxy, N,N-di-n-octylaminocarbonyloxy and N-n-octylcarbamoyloxy), an alkoxycarbonyloxy group (examples of the alkoxycarbonyloxy group include substituted or unsubstituted alkoxycarbonyloxy groups preferably having from 2 to 30 carbon atoms, e.g., methoxycarbonyloxy, ethoxycarbonyloxy, t-butoxycarbonyloxy and n-octylcarbonyloxy), an aryloxycarbonyloxy group (examples of the aryloxycarbonyloxy group include substituted or unsubstituted aryloxycarbonyloxy groups preferably having from 7 to 30 carbon atoms, e.g., phenoxycarbonyloxy, p-methoxyphenylcarbonyloxy and p-n-hexadecyloxyphenoxycarbonyloxy), an amino group (preferable examples of the amino group include an amino group, a substituted or unsubstituted alkylamino group having from 1 to 30 carbon atoms, and a substituted or unsubstituted anilino group having from 6 to 30 carbon atoms, e.g., methylamino, dimethylamino, anilino, N-methylanilino and diphenylamino), an acylamino group (preferable examples of the acylamino group include formylamino, a substituted or unsubstituted alkylcarbonylamino group having from 1 to 30 carbon atoms, and a substituted or unsubstituted arylcarbonylamino group, e.g., formylamino, acetylamino, pivaloylamino, lauroylamino, benzoylamino and 3,4,5-tri-n-octyloxyphenylcarbonylamino), an aminocarbonylamino group (preferable examples of the group include substituted or unsubstituted aminocarbonylamino group having from 1 to 30 carbon atoms, e.g., carbamoylamino, N,N-dimethylaminocarbonylamino, N,N-diethylaminocarbonylamino and morpholinocarbonylamino), an alkoxycarbonylamino group (preferable examples of the alkoxycarbonylamino group include substituted or unsubstituted alkoxycarbonylamino groups having from 2 to 30 carbon atoms, e.g., methoxycarbonylamino, ethoxycarbonylamino, t-butoxycarbonylamino, n-octadecyloxycarbonylamino and N-methyl-methoxycarbonylamino), an aryloxycarbonylamino group (preferable examples of the ryloxycarbonylamino group include substituted or unsubstituted aryloxycarbonylamino groups having from 7 to 30 carbon atoms, e.g., phenoxycarbonylamino, p-chlorophenoxycarbonylamino and m-(n-octyloxy)phenoxycarbonylamino), a sulfamoylamino group (preferable examples of the sulfamoylamino group include substituted or unsubstituted sulfamoylamino groups having from 0 to 30 carbon atoms, e.g., sulfamoylamino, N,N-dimethylaminosulfonylamino and N-n-octylaminosulfonylamino), an alkyl or arylsulfonylamino group (preferable examples of the alkyl or arylsulfonylamino group include substituted or unsubstituted alkylsulfonyl amino groups having from 1 to 30 carbon atoms, and substituted or unsubstituted arylsulfonylaminogroups having from 6 to 30 carbon atoms, e.g., methylsulfonylamino, butylsulfonylamino, phenylsulfonylamino, 2,3,5-trichlorphenylsulfonylamino and p-methylphenylsulfonylamino), a mercapto group, an alkylthio group (preferable examples of the alkylthio group include substituted or unsubstituted alkylthio groups having from 1 to 30 carbon atoms, e.g., methylthio, ethylthio and n-hexadecylthio), an arylthio group (preferable examples of the arylthio group include substituted or unsubstituted arylthio groups having from 6 to 30 carbon atoms, e.g., phenylthio, p-chlorophenylthio and m-methoxyphenylthio), a heterocyclic-thio group (preferable examples of the heterocyclic-thio group include substituted or unsubstituted heterocyclic-thiogroupshaving from 2 to 30 carbonatoms, e.g., 2-benzothiazolylthio and 1-phenyltetrazol-5-ylthio), a sulfamoyl group (preferable examples of the sulfamoyl group include substituted or unsubstituted sulfamoyl groups having from 0 to 30 carbon atoms, e.g., N-ethylsulfamoyl, N-(3-dodecyloxypropyl)sulfamoyl, N,N-dimethylsulfamoyl, N-acetylsulfamoyl and N-benzoylsulfamoyl, N-(N'-phenylcarbamoyl)sulfamoyl), a sulfo group, an alkyl or arylsulfinyl group (preferable examples of the alkyl or arylsulfinyl group include substituted or unsubstituted alkylsulfinyl groups having from 1 to 30 carbon atoms, and substituted or unsubstituted arylsulfinyl groups having from 6 to 30 carbon atoms, e.g., methylsulfinyl, ethylsulfinyl, phenylsulfinyl and p-methylphenylsulfinyl), an alkyl or arylsulfonyl group (preferable examples of the alkyl or arylsulfonyl group include substituted or unsubstituted alkylsulfonyl groups having from 1 to 30 carbon atoms, and substituted or unsubstituted arylsulfonyl groups having from 6 to 30 carbon atoms, e.g., methylsulfonyl, ethylsulfonyl, phenylsulfonyl and p-methylphenylsulfonyl), an aryloxysulfinyl group (preferable examples of the aryloxysulfinyl group include substituted or unsubstituted aryloxysulfinyl groups having from 7 to 30 carbon atoms, e.g., phenoxysulfinyl, o-chlorophenoxysulfinyl, m-nitrophenoxysulfinyl and p-t-butylphenoxysulfinyl), an alkoxysulfinyl group (preferable examples of the alkoxysulfinyl group include substituted or unsubstituted alkoxysulfinyl groups preferably having from 2 to 30 carbon atoms, e.g., methoxysulfinyl, ethoxysulfinyl, t-butoxysulfinyl and n-octadecyloxysulfinyl), an aryloxysulfonyl group (preferable examples of the aryloxysulfonyl group include substituted or unsubstituted aryloxysulfonyl groups having from 7 to 30 carbon atoms, e.g., phenoxysulfonyl, o-chlorophenoxysulfonyl, m-nitrophenoxysulfonyl and p-t-butylphenoxysulfonyl), an alkoxysulfonyl group (preferable examples of the alkoxysulfonyl group include substituted or unsubstituted alkoxysulfonyl groups having from 2 to 30 carbon atoms, e.g., methoxysulfonyl, ethoxysulfonyl, t-butoxysulfonyl and n-octadecyloxysulfonyl), an acyl group (preferable examples of the acyl group include a formyl group, substituted or unsubstituted alkylcarbonyl groups having from 2 to 30 carbon atoms, and substituted or unsubstituted arylcarbonyl groups having from 7 to 30 carbon atoms, e.g., acetyl, pivaloyl, 2-chloroacetyl, stearoyl, benzoyl and p-n-octyloxyphenylcarbonyl), an aryloxycarbonyl group (preferable examples of the aryloxycarbonyl group include substituted or unsubstituted aryloxycarbonyl groups having from 7 to 30 carbon atoms, e.g., phenoxycarbonyl, o-chlorophenoxycarbonyl, m-nitrophenoxycarbonyl and p-t-butylphenoxycarbonyl), an alkoxycarbonyl group (preferable examples of the alkoxycarbonyl group include substituted or unsubstituted alkoxycarbonyl groups having from 2 to 30 carbon atoms, e.g., methoxycarbonyl, ethoxycarbonyl, t-butoxycarbonyl and n-octadecyloxycarbonyl), a carbamoyl group (preferable examples of the carbamoyl group include substituted or unsubstituted carbamoyl groups having from 1 to 30 carbon atoms, e.g., carbamoyl, N-methylcarbamoyl, N,N-dimethylcarbamoyl, N,N-di-n-octylcarbamoyl and N-(methylsulfonyl)carbamoyl), an aryl or heterocyclic azo group (preferable examples of the aryl or heterocyclic azo group include substituted or unsubstituted arylazo groups having from 6 to 30 carbon atoms, and substituted or unsubstituted heterocyclic-azo group having from 3 to 30 carbon atoms, e.g., phenylazo, p-chlorophenylazo and 5-ethylthio-1,3,4-thiadiazol-2-ylazo), an imide group (preferable examples of the imide group include N-succinimide and N-phthalimide), a phosphino group (preferable examples of the phosphino group include substituted or unsubstituted phosphino groups having from 2 to 30 carbon atoms, e.g., dimethylphosphino, diphenylphosphino and methylphenoxyphosphino), a phosphinyl group (preferable examples of the phosphinyl group include substituted or unsubstituted phosphinyl groups having from 2 to 30 carbon atoms, e.g., phosphinyl, dioctyloxyphosphinyl and diethoxyphosphinyl), a phosphinyloxy group (preferable examples of the phosphinyloxy group include substituted or unsubstituted phosphinyloxy groups having from 2 to 30 carbon atoms, e.g., diphenoxyphosphinyloxy and dioctyloxyphosphinyloxy), a phosphinylamino group (preferable examples of the phosphinylamino group include substituted or unsubstituted phosphinylamino groups preferably having from 2 to 30 carbon atoms, e.g., dimethoxyphosphinylamino and dimethylaminophosphinylamino), and a silyl group (preferable examples of the silyl group include substituted or unsubstituted silyl groups having from 3 to 30 carbon atoms, e.g., trimethylsilyl, t-butyldimethylsilyl and phenyldimethylsilyl).

Of the substituents mentioned above, those having hydrogen atom(s) may be further substituted by removing the hydrogen atom(s) and substituting the removed hydrogen atom(s) with any other substituent. The any other substituent may include aforementioned groups. Examples of the substituted substituents include an alkylcarbonylaminosulfonyl group, an arylcarbonylaminosulfonyl group, an alkylsulfonylaminocarbonyl group and an arylsulfonylaminocarbonyl group. Concrete examples thereof include a methylsulfonylcarbonyl group, a p-methylphenylsulfonylaminocarbonyl group, an acetylaminosulfonyl group, and a benzoylaminosulfonyl group.

When at least one of $R^1$ and $R^2$ is a substituent, the substituent is preferably a halogen atom, an alkyl group, an alkoxy group, cyano group or nitro group. More preferably, the substituent is ahalogen atom, an alkyl group oran alkoxy group.

Preferably, at least one of $R^1$ and $R^2$ is a substituent mentioned above other than a hydrogen atom. More preferably, both $R^1$ and $R^2$ are substituents other than hydrogen atom. In a case where both $R^1$ and $R^2$ are substituents mentioned above, it is preferable that each of $R^1$ and $R^2$ is independently a halogen atom, an alkyl group or an alkoxy group. Most preferably, both $R^1$ and $R^2$ are methyl groups.

In general formula (I), $R^3$ represents a substituent. Examples of the substituent include those substituents mentioned above for $R^1$ and $R^2$. m indicates an integer from 0 to 3. When m is neither 0 nor 1, or that is to say, when m is 2 or greater, $R^3$'s may be the same as or different from each other and may be bonded to each other to form a condensed ring. $R^3$ may be bonded to $R^1$ or $R^2$ to form a condensed ring.

Preferably, $R^3$ is an electron-attractive substituent having a Hammett's substituent constant $\sigma_p$ of no less than 0 (more preferably from 0 to 1.5). The Hammett's substituent constant $\sigma_p$ is described in detail in documents, for example, in *Hamettosoku—Kôzô To Han'nôsei (Hammett's Rule—Structure and Reactivity)* written by Naoki Inamoto (published by Maruzen); *Shinjikken Kagaku Kôza 14, Yûki Kagôbutsu No Gôsei To Han'nôV (Novel Experimental Chemistry Lecture 14, Synthesis and Reaction V of Organic Compounds)*, p. 2605 (edited by the Chemical Society of Japan, published by Maruzen); *Riron Yûki Kagaku Kaisetsu (Theoretical Organic Chemistry Handbook)* written by Tadao Nakaya, p. 217 (published by Tokyo Kagaku Dojin); *Kemikaru Rebyû(Chemical Review)*, vol. 91, pp. 165–195 (1991).

More preferably, $R^3$ is an electron-attractive substituent having a Hammett's substituent constant $\sigma_p$ of no less than 0.1 (more preferably from 0.1 to 1.5). Still more preferably, $R^3$ is an electron-attractive substituent having $\sigma_p$ of not less than 0.3 (more preferably from 0.3 to 1.0). Preferable examples of $R^3$ include a halogen atom, an acyl group, an alkoxycarbonyl group, an aryloxycarbonyl group, a carbamoyl group, an alkylsulfonyl group, an arylsulfonyl group, an alkoxysulfonyl group, an aryloxysulfonyl group, a sulfamoyl group, an alkylsulfinyl group, an arylsulfinyl group, an alkoxysulfinyl group, an aryloxysulfinyl group, a carboxyl group, a sulfo group, a cyano group and a nitro group. More preferably, $R^3$ is a halogen atom, an alkylsulfonyl group, an arylsulfonyl group, a sulfamoyl group, a cyano group or a nitro group.

In formula (I), $R^4$ represents an aryl group or a heterocyclic group. Concretely, $R^4$ represents an aryl group (preferable examples thereof include substituted or unsubstitutedaryl groups having from 6 to 30 carbon atoms, e.g., phenyl, p-tolyl, naphthyl, m-chlorophenyl, and o-hexadecanoylaminophenyl), or a heterocyclic group (examples thereof include monovalent groups derived from a substituted or unsubstituted, aromatic or non-aromatic heterocyclic compound preferably having 5 or 6 members heterocyclic ring by removing one hydrogen atom from the compound; examples of the hetero atom comprised in the hetero ring include nitrogen, oxygen, sulfur and phosphorus; more preferably, this heterocyclic group is a 5-membered or 6-membered aromatic heterocyclic group having from 3 to 30 carbon atoms, e.g., 2-furyl, 2-thienyl, 2-pyridyl, 2-pyrimidinyl, and 2-benzothiazolyl). $R^4$ may have one or more substitutents. Examples of the substituent include the substituents mentioned above for $R^1$ and $R^2$. Preferably, $R^4$ is an aryl group, and is more preferably substituted with ahalogen atom, an alkoxy group or an aryloxy group at an ortho-position thereof relative to an anilide nitrogen to which the $R^4$ is bonded.

In general formula (I), $R^5$ and $R^6$ each independently represent a hydrogen atom or a substituent. Examples of the substituent for $R^5$ and $R^6$ include the substituents mentioned above for $R^1$ and $R^2$. Preferably, $R^5$ and $R^6$ represent substituents other than hydrogen atom, and more preferably represent alkyl groups. $R^5$ and $R^6$ may have one or more substitutents. Examples of the substituent for $R^5$ and $R^6$ include the substituents mentioned above for $R^1$ and $R^2$. More preferably, $R^5$ and $R^6$ each represent amethyl group, an ethyl group, a 2-hydroxyethyl group or a 2-methanesulfonylaminoethyl group.

In general formula (I), $R^7$ represents a substituent. Examples of the substituent include the substituents mentioned above for $R^1$ and $R^2$. n indicates an integer from 0 to 4. When n is neither 0 nor 1, or that is to say, when n is 2 or greater, $R^7$'s may be the same as or different from each other and may be bonded to each other to form a condensed ring. $R^7$ may be bonded to $R^5$ or $R^6$ to form a condensed ring. $R^5$ and $R^6$ may be bonded to each other to form a ring. n is preferably 0 or 1, and is more preferably 1. $R^7$ is preferably an alkyl group, an alkoxy group or an acylamino group, and is more preferably an alkyl group. More preferably, $R^7$ is a methyl group that is ortho-positioned relative to an azomethine nitrogen in the compound represented by general formula (I). That is, $R^7$ is preferably a methyl group that is provide at ortho-positione with respect to nitrogen of an azomethine portion in the compound represented by general formula (I)

Preferred examples of the compound represented by formula (I) of the present invention are shown below. However, the present invention is not limited thereto.
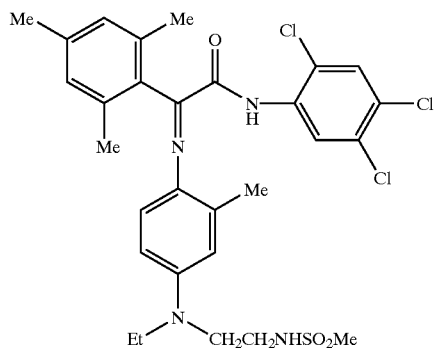
(1)
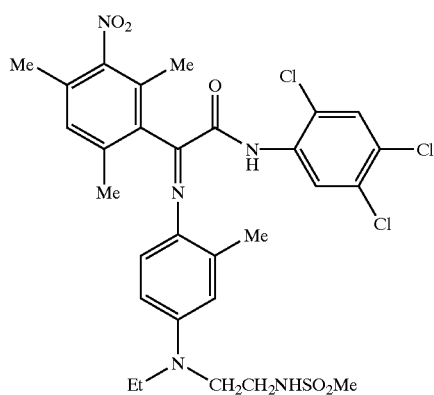
(2)
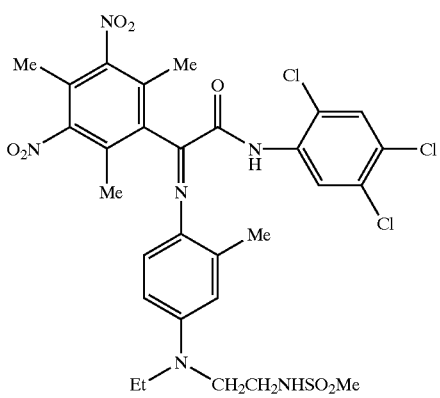
(3)
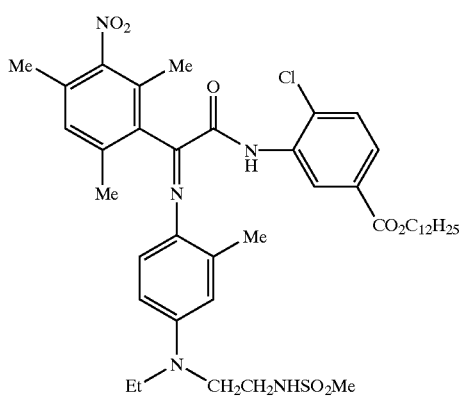
(4)
-continued
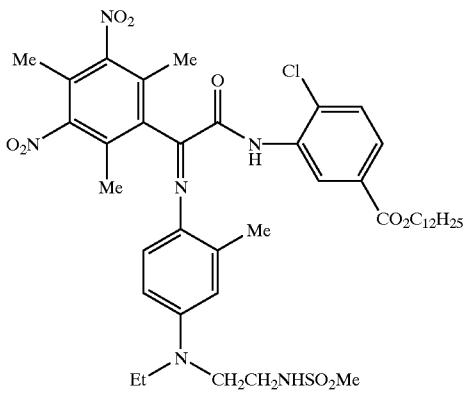
(5)
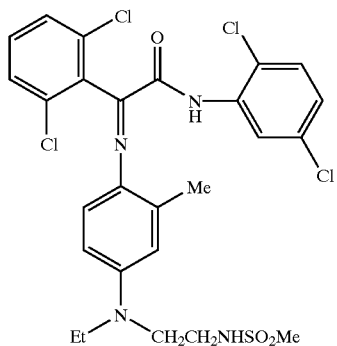
(6)
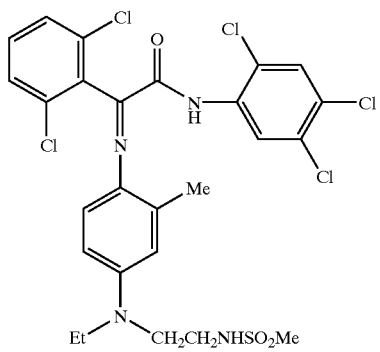
(7)
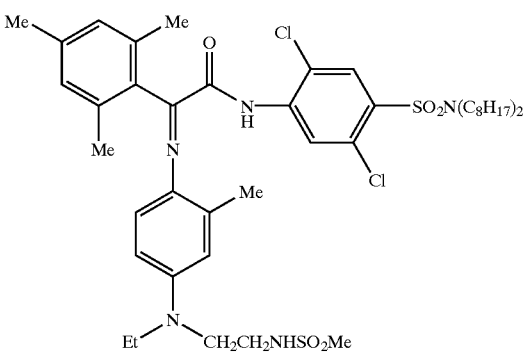
(8)

-continued
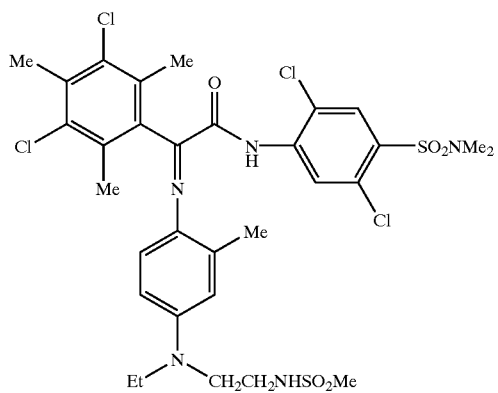
(9)
(10)
(11)
(12)
-continued
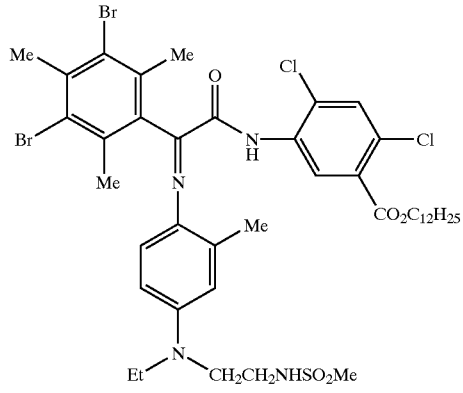
(13)
(14)
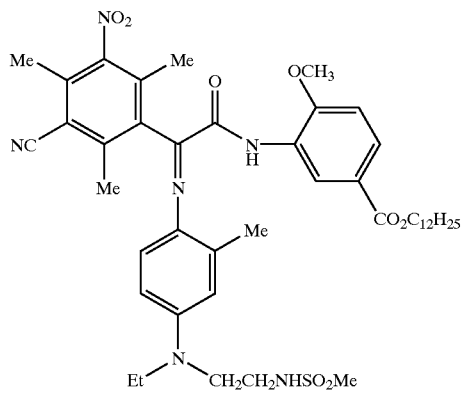
(15)
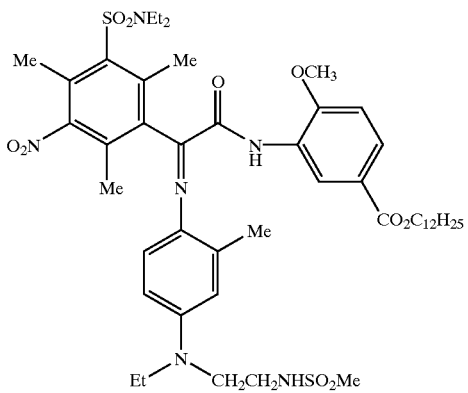
(16)
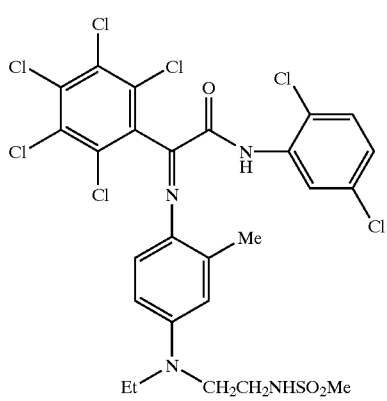

(17)
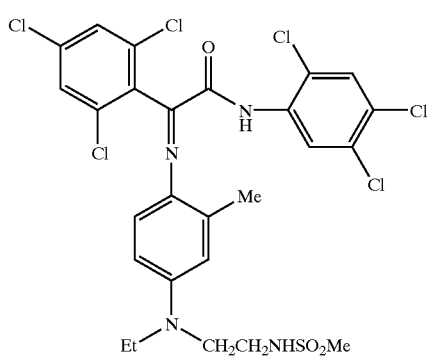
(18)
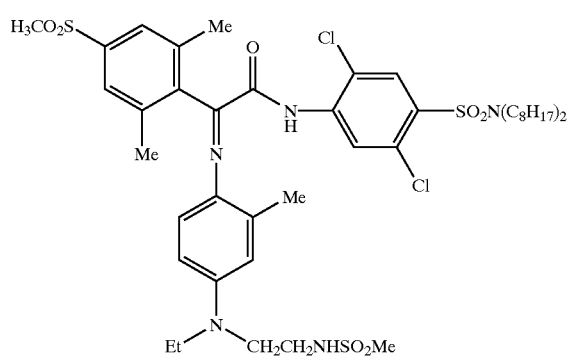
(19)
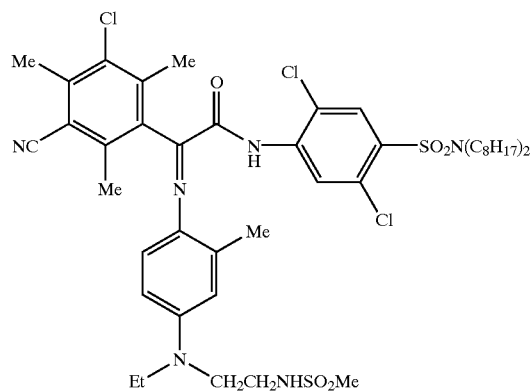
(20)
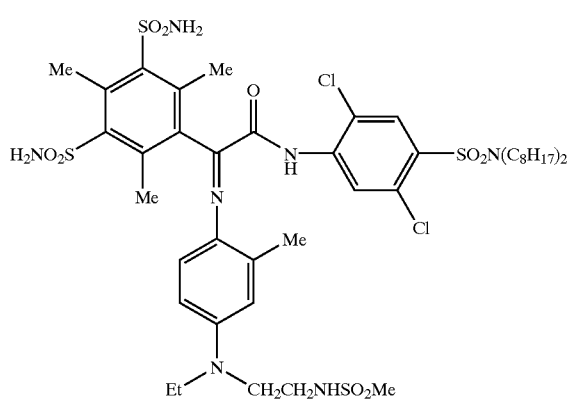
(21)
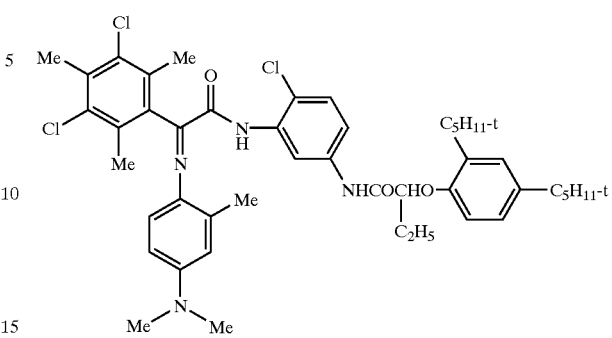
(22)
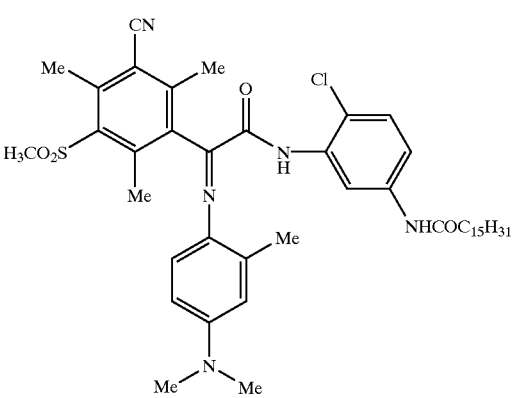
(23)
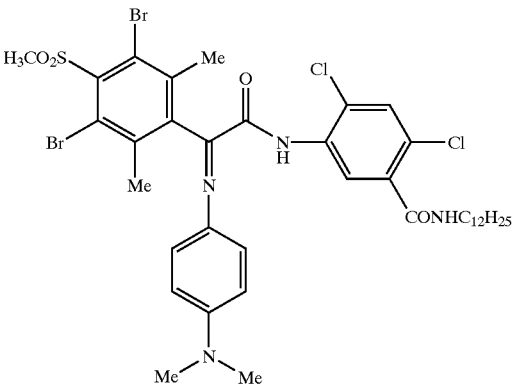
(24)
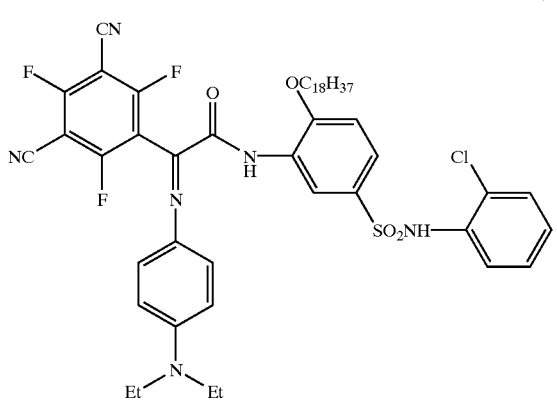

(25) 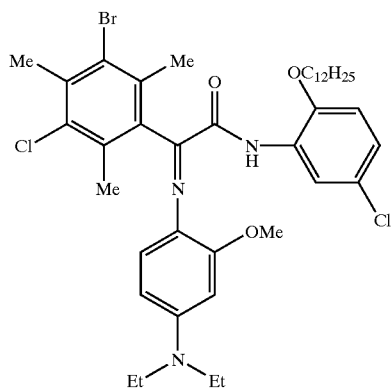
(26) 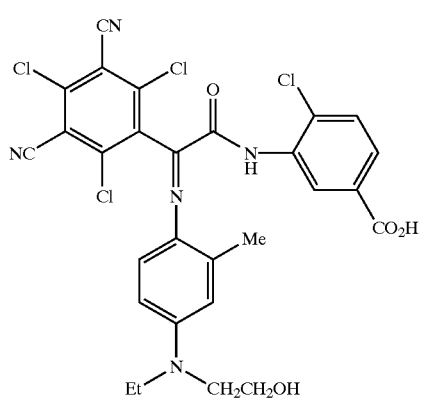
(27) 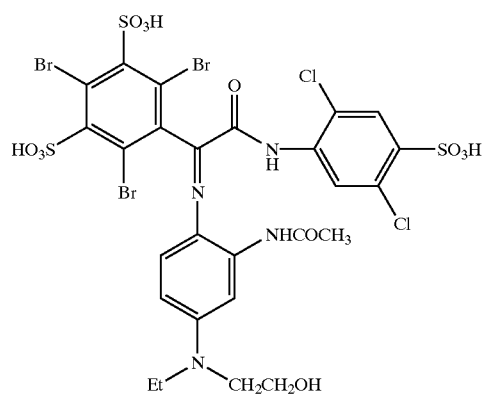
(28) 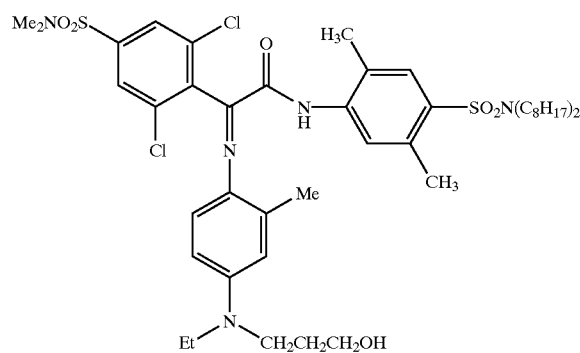
(29) 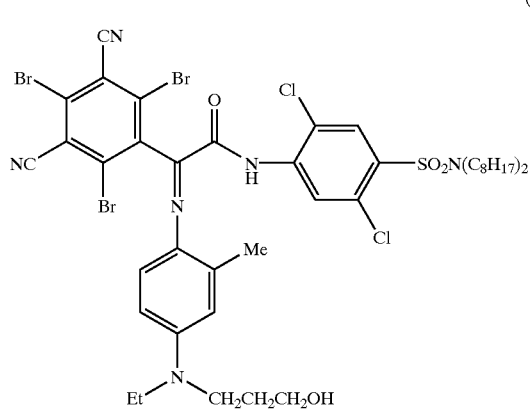
(30) 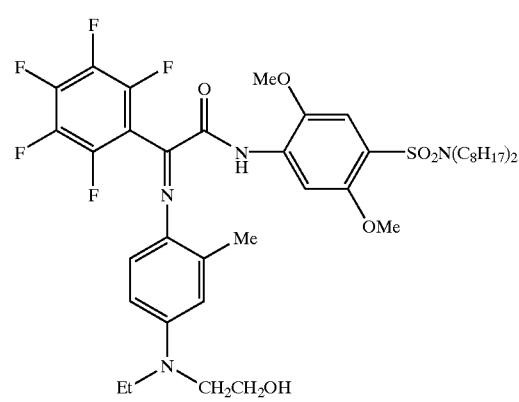
(31) 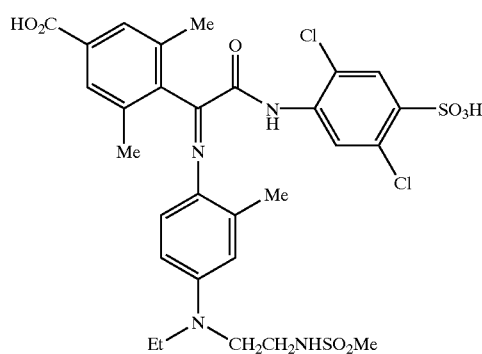
(32) 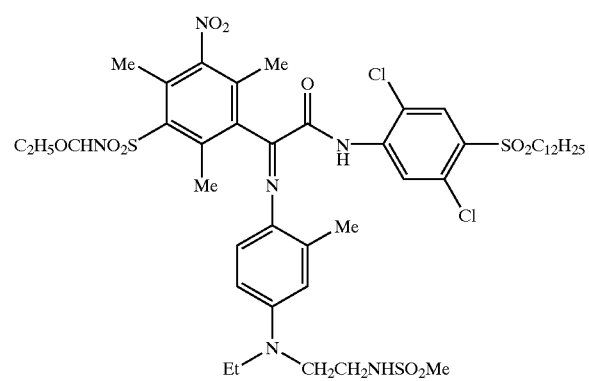

-continued (33), (34), (35), (36), (37), (38), (39), (40)

-continued
(41)
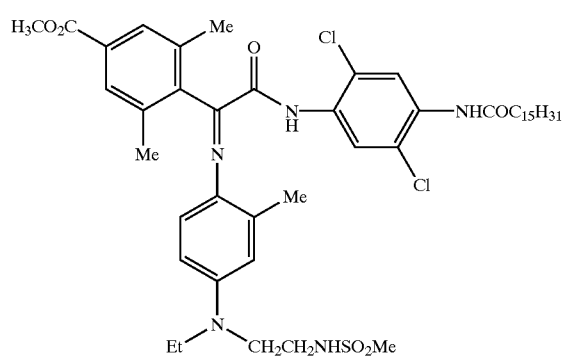
(42)
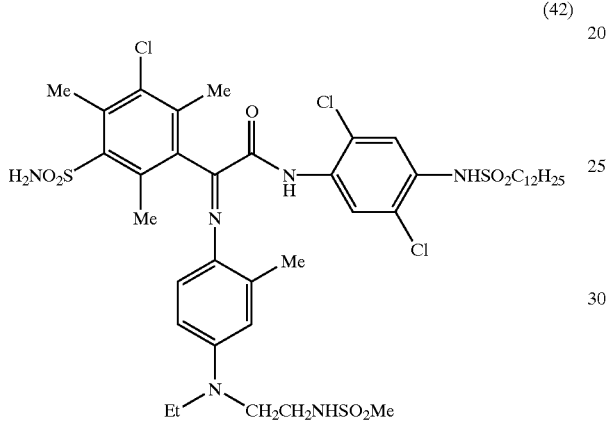
(43)
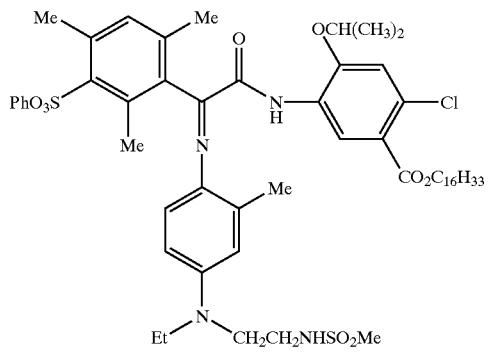
(44)
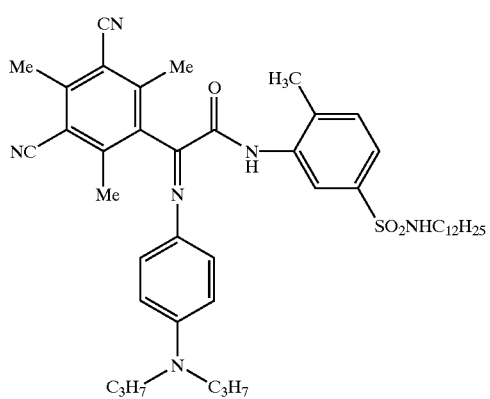
-continued
(45)
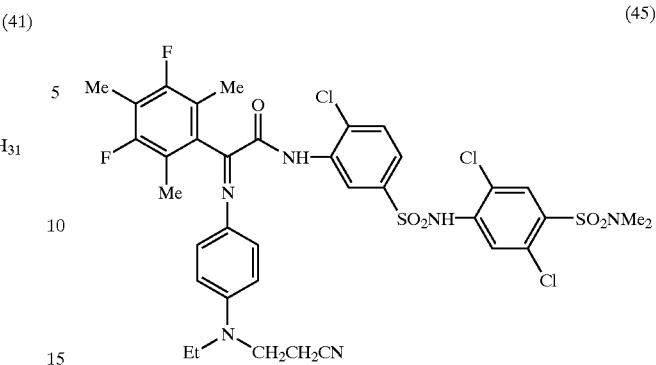
(46)
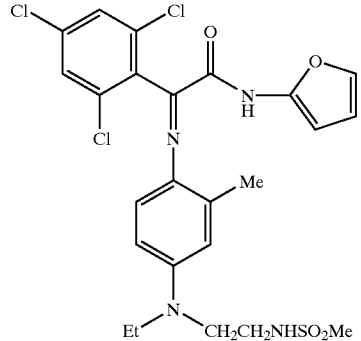
(47)
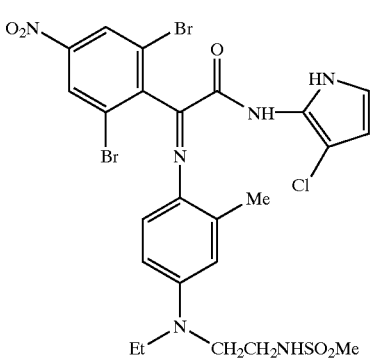
(48)
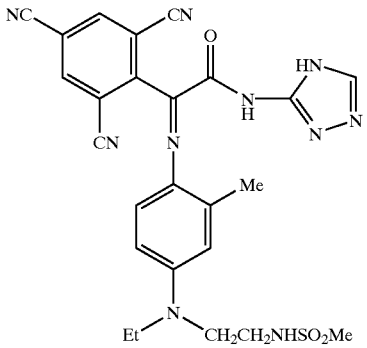

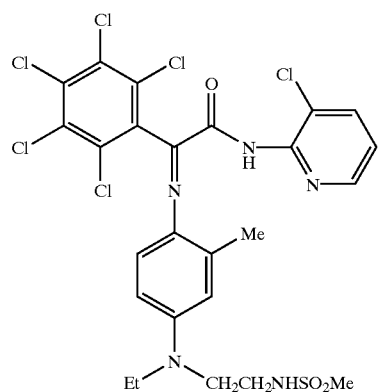
(49)
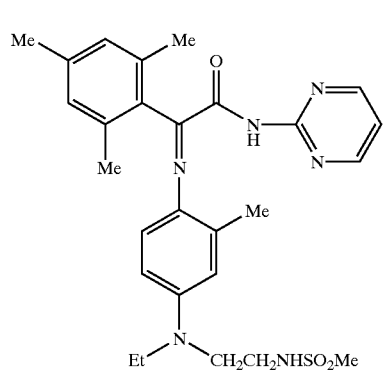
(50)
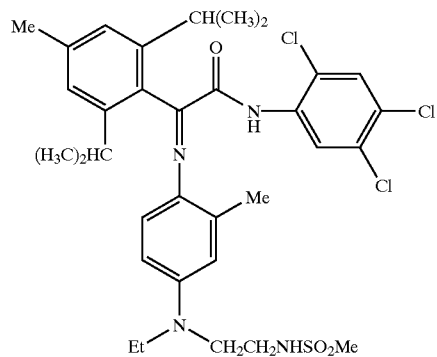
(51)
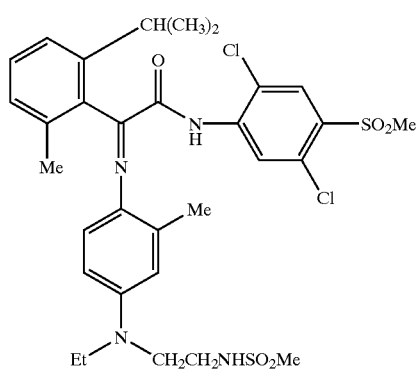
(52)
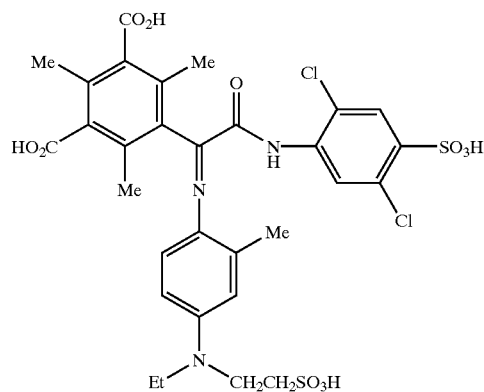
(53)
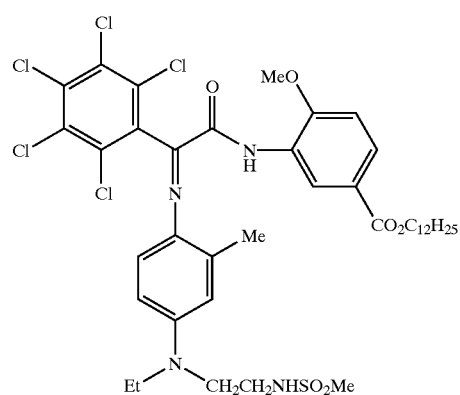
(54)
(55)

(56)
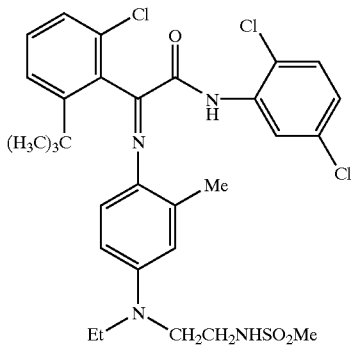

(57)
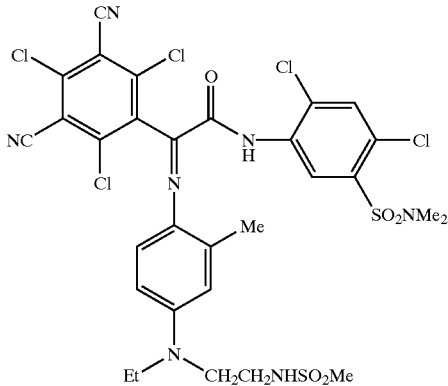

(58)
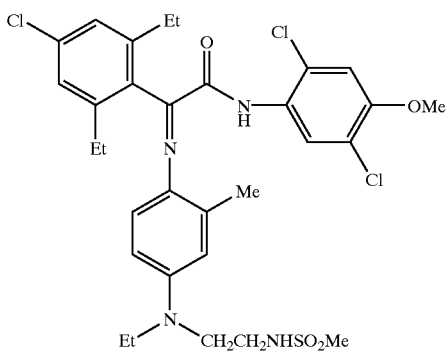

(59)
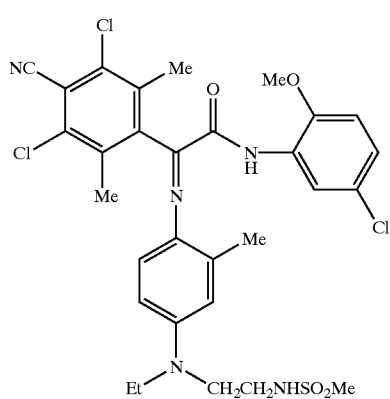

(60)
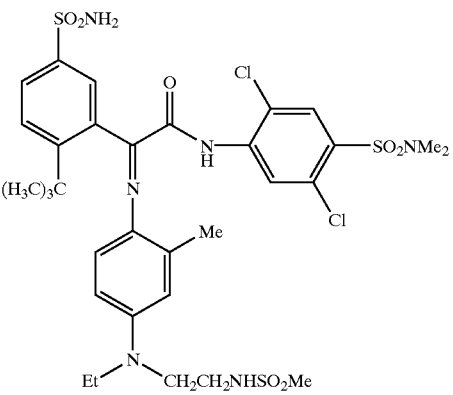

In the following description, when the compound exemplified above is referred to, the compounds is designated as "Compound (X)" in which X indicates the parenthesized number of each compound.

The compound represented by general formula (I) can be produced through a coupling reaction of a compound represented by the following general formula (II) with an oxidation product of a p-phenylenediamine derivative, and more preferably with an oxidation product of an N,N-disubstituted p-phenylenediamine derivative.

General formula (II)

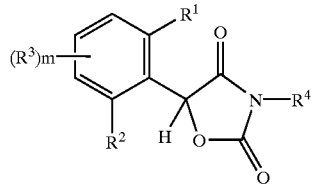

In general formula (II), $R^1$ and $R^2$ each independently represent a hydrogen atom or a substituent; $R^3$ represents a substituent; m indicates an integer from 0 to 3; when m is not 0 or 1, or that is to say, when m is 2 or greater, $R^3$'s may be the same as or different from each other and may be bonded to each other to form a condensed ring; $R^3$ may be bonded to $R^1$ or $R^2$ to form a condensed ring; and $R^4$ represents an aryl group or a heterocyclic group. The details of $R^1$, $R^2$, $R^3$, $R^4$ and m are as described above for general formula (I). That is, the details of $R^1$, $R^2$, $R^3$, $R^4$ and m are the same as $R^1$, $R^2$, $R^3$, $R^4$ and m described for general formula (I).

Specifically, the dye represented by general formula (I) can be synthesized from a compound represented by general formula (II) and a compound represented by the following general formula (A), as shown below. Precisely, one hydrogen atom is dissociated from the compound represented by general formula (II), the compound is then coupled with an oxidation product of the compound (A), which has been oxidized with an oxidizing agent, and $CO_2$ is removed from the coupled product to form an azomethine dye represented by general formula (I).

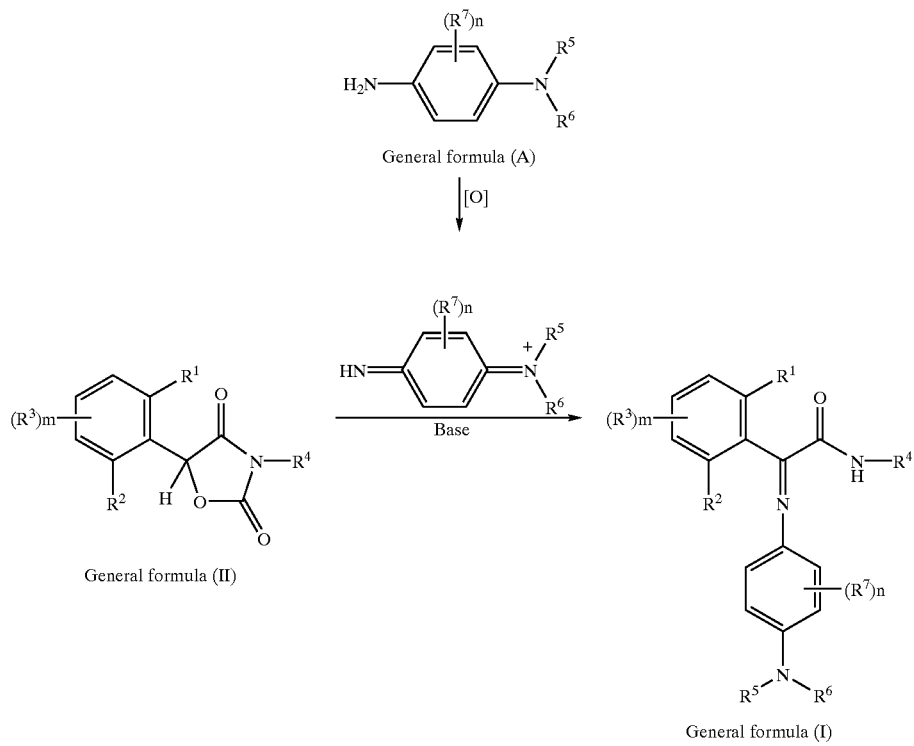

In general formula (A), $R^5$ and $R^6$ each independently represent a hydrogen atom or a substituent; $R^7$ represents a substituent; n indicates an integer from 0 to 4; when n is not 0 or 1, or that is to say; when n is 2 or greater, $R^7$'s may be the same as or different from each other and may be bonded to each other to form a condensed ring; $R^7$ may be bonded to $R^5$ or $R^6$ to form a condensed ring; and $R^5$ and $R^6$ may be bonded to each other to form a ring.

The details of $R^5$, $R^6$, $R^7$ and n are as described above for general formula (I).

The compound represented by general formula (II) can be synthesized by various known methods. For example, it can be produced according to the methods described in examples described below.

The azomethine yellow dye compound of the present invention can be used as yellow dye for silver halide photographic photosensitive materials, yellow dye for inkjet or thermal transfer printing materials, yellow dye for toner in electrophotography, yellow dye for prints, yellow dye for color proofs, yellow dye for optical memory media, yellow dye for organic electroluminesence elements, filter dye for solid-state image pickup tubes or color liquid-crystal televisions, and as an intermediate used in the production thereof.

The azomethine yellow dye compound of the present invention has a large absorption coefficient, and color fastness thereof is good. Therefore, the dye compound is especially useful in image recording and has the merit such that an amount thereof to be used can be reduced as compared with conventional dyes. Accordingly, the dye compound is preferably used as yellow dye for silver halide photographic photosensitive materials, yellow dye for inkjet or thermal transfer printing materials, yellow dye for prints, and yellow dye for color proofs, and more preferable used as yellow dye for silver halide photographic photosensitive materials including color proofs and to yellow dye for inkjet or thermal transfer printing materials.

EXAMPLES

The present invention is described in further detail by way of the following examples. However, the scope of the present invention is not restricted thereto.

Example 1

Production Example 1

Production of Compound (6)

Compound (6) can be synthesized according to the reaction process shown below.

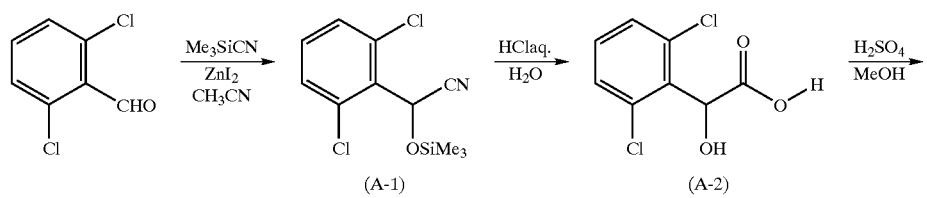

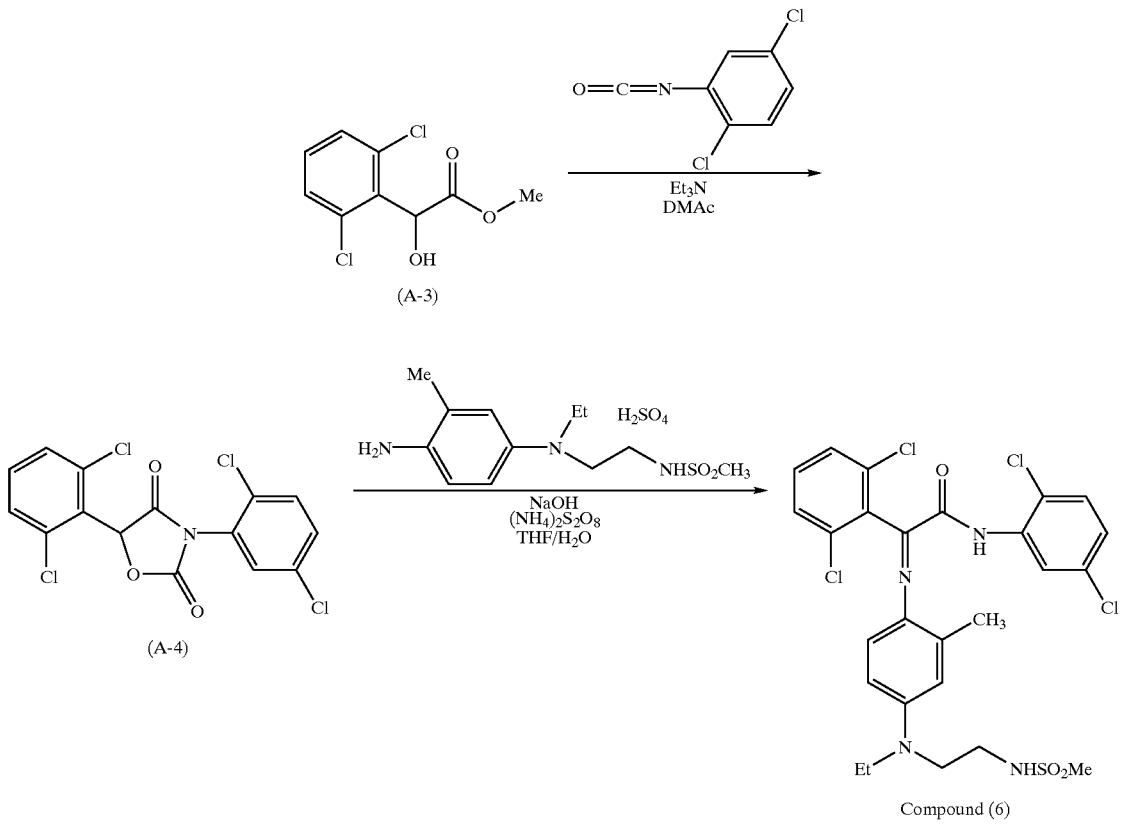

In a nitrogen atmosphere at 0° C., 7.4 g of trimethylsilylcyanide was dropwise added to 50 ml of an acetonitrile solution comprising 0.73 g of zinc iodide and 11.9 g of 2,6-dichlorobenzaldehyde. Restored to room temperature from 0° C., the solution was stirred for 2 hours. Then, the resulting solution was poured into water containing ice, ethyl acetate was further added thereto and an extraction was conducted with the ethyl acetate. An obtained organic layer was washed with a saturated saline solution and then dried with anhydrous magnesium sulfate. The solvent comprised therein was evaporated away under reduced pressure, and a liquid of Compound (A-1) was obtained.

10 ml of water was added to the liquid, and 150 ml of 35% hydrochloric acid was then added thereto. This resulting solution was stirred for 2 hours while being heated to reflux. Then the resulting solution was cooled to 0° C., and a 2% aqueous solution of potassium hydroxide was added thereto to give the solution weak alkalinity. This solution was phase-separated with ethyl acetate added thereto, and an obtained aqueous phase was weakly acidified with 1 N hydrochloric acid and then extracted with ethyl acetate. An obtained organic layer was dried with anhydrous magnesium sulfate, and the solvent comprised therein was evaporated away under reduced pressure. As a result, 12.4 g of Compound (A-2) was obtained.

10 g of Compound (A-2) was dissolved in 70 ml of methanol, and 4 or 5 drops of concentrated sulfuric acid were added thereto. The resulting solution was stirred for 2 hours, while being heated to reflux. After the solution was cooled, the solution was extracted with a 10% aqueous solution of potassium carbonate and ethyl acetate added thereto. An obtained organic layer was washed with a saturated saline solution and dried with anhydrous magnesium sulfate. The solvent comprised therein was evaporated away under reduced pressure, and 9.1 g of Compound (A-3) was obtained.

80 ml of an N,N-dimethylacetamide solution comprising 9 g of Compound (A-3), 7.2 g of 2,5-dichlorophenyl isocyanate and 3.9 g of triethylamine, was heated to 110° C., and kept stirred for 3 hours. After the solution was cooled, the solution was extracted with water and ethyl acetate added thereto, and an obtained organic layer was washed with a saturated saline solution and then dried with anhydrous magnesium sulfate. A solvent comprised therein was evaporated away under reduced pressure, and the residue was crystallized from a mixed solvent of ethyl acetate and hexane to obtain 8.2 g of Compound (A-4).

A solution in which 1.8 g of ammonium persulfate had been dissolved in 15 ml of water was gradually added to a mixture comprising 3.0 g of Compound (A-4), 1.5 g of N-ethyl-N-(2-methanesulfonamidoethyl)-3-methyl-4-aminoaniline sulfate, 40 ml of THF and 40 ml of 1 N aqueous solution of sodium hydroxide, by stirring at room temperature. After being stirred for 10 minutes, the resulting solution was extracted with water and ethyl acetate added thereto, and an obtained organic layer was washed with a saturated saline solution and then dried with anhydrous magnesium sulfate. The solvent comprised therein was evaporated away under reduced pressure, and the residue was purified through a silica gel chromatography to obtain 0.92 g of Compound (6). This is Dye (6) of the present invention.

Production Example 2

Production of Compound (1)

Compound (1) can be synthesized according to the reaction process shown below.

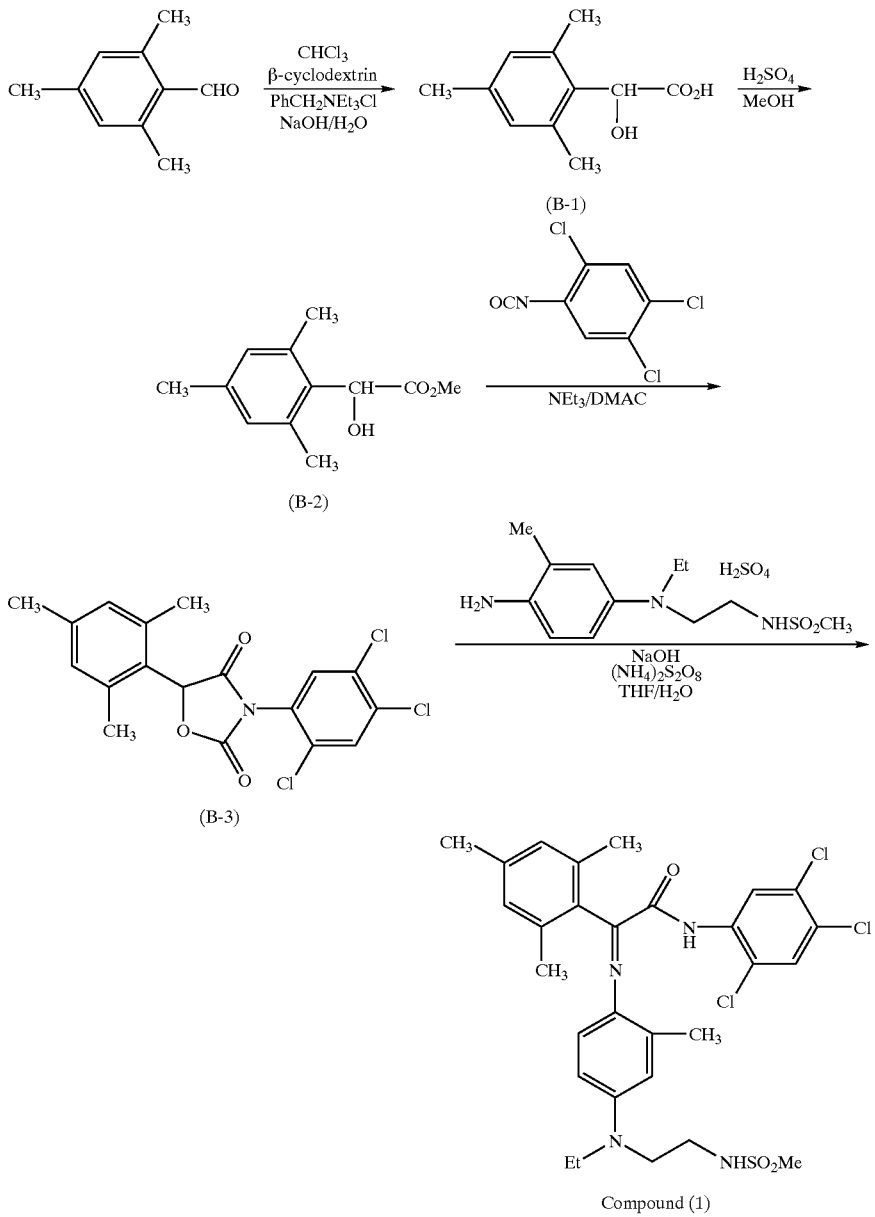

Compound (1)

74.1 g of mesitylene, 11.4 g of β-cyclodextrin, 5.7 g of benzyltriethylammonium chloride and 100 g of chloroform were mixed, and stirred at 50° C. for 20 minutes. A solution comprising 100 g of sodium hydroxide and 100 ml of water was dropwise added to the mixture over a period of 30 minutes while the mixture was cooled with water such that a temperature thereof was maintained at 50 to 60° C. The resulting solution was stirred at 50° C. for 4 hours, then heated to reflux for 5 hours, and phase-separated with ethyl acetate and water, which were added thereto. An obtained aqueous layer was acidified by adding hydrochloric acid, and then extracted with ethyl acetate. An obtained organic layer was dried with anhydrous magnesium sulfate, and a solvent comprised therein was evaporated away under reduced pressure. The residue was crystallized with a mixed solvent of ethyl acetate and hexane, and 36.2 g of Compound (B-1) was obtained.

Next, 15.5 g of Compound (B-1) and 1.5 ml of concentrated sulfuric acid were dissolved in 150 ml of methanol, and heated to reflux for 6 hours. The resulting solution was extracted with ethyl acetate and water added thereto, and an obtained organic layer was washed with aqueous sodium bicarbonate and a saturated saline solution and then dried with anhydrous magnesium sulfate. A solvent comprised therein was evaporated away under reduced pressure, and the residue was crystallized with a mixed solvent of ethyl acetate and hexane to obtain 14.6 g of Compound (B-2).

7.0 ml of triethylamine was dropwise added to 100 ml of an N,N-dimethylacetamide solution containing 10.4 g of Compound (B-2) and 12.2 g of 2,4,5-trichlorophenyl isocyanate, over a period of 30 minutes. This solution was stirred at room temperature for 1.5 hours and then at 80° C. for 30 minutes. 2.5 ml of triethylamine was added thereto, and the solution was further stirred at 115° C. for 1.5 hours. This solution was extracted with ethyl acetate and water added thereto. An obtained organic layer was washed with diluted hydrochloric acid and a saturated saline solution, and then dried with anhydrous magnesium sulfate. A solvent comprised therein was evaporated away under reduced pressure, and the residue was crystallized with a mixed solvent of ethyl acetate and hexane to obtain 5.5 g of Compound (B-3).

A solution of 1.8 g of ammonium persulfate dissolved in 15 ml of water was gradually added to a mixture of 3.0 g of Compound (B-3), 1.5 g of N-ethyl-N-(2-methanesulfonamidoethyl)-3-methyl-4-aminoaniline sulfate, 40 ml of THF and 40 ml of 1 N aqueous solution of sodium hydroxide while the mixture was stirred at room temperature. The resulting solution was stirred for 10 minutes, and extracted with water and ethylacetate addedt hereto. An obtained organic layer was washed with a saturated saline solution and then the dried with anhydrous magnesium sulfate. A solvent comprised therein was evaporated away under reduced pressure, and the residue was purified through silica gel chromatography to obtain 0.70 g of Compound (1). This is Dye (1) of the present invention.

Production Example 3

Production of Compound (2)

Compound (2) can be synthesized according to the reaction process shown below.

30 ml of concentrated nitric acid (specific gravity: 1.38) was dropwise added to 30 ml of concentrated sulfuric acid while the mixture was cooled with ice, and the mixture was stirred for 10 minutes. A solution of 3.9 g of Compound (B-3) dissolved in 15 ml of methylene chloride was dropwise added thereto over a period of 5 minutes, and then stirred at room temperature for 1 hour. The reaction mixture was poured into water with ice, and extracted with ethyl acetate. An obtained organic layer was washed with aqueous sodium bicarbonate and a saturated saline solution, and then dried with anhydrous magnesium sulfate. A solvent comprised therein was evaporated away under reduced pressure, and the residue was purified through column chromatography and then crystallized with a mixed solvent of ethyl acetate and hexane to obtain 3.4 g of Compound (C-3).

A solution of 1.8 g of ammonium persulfate dissolved in 15 ml of water was gradually added to a mixture of 3.0 g of Compound (C-3), 1.5 g of N-ethyl-N-(2-methanesulfonamidoethyl)-3-methyl-4-aminoaniline sulfate, 40 ml of THF and 40 ml of 1 N aqueous solution of potassium hydroxide while the mixture was stirred at room temperature. After being stirred for 10 minutes, the resulting solution was extracted with water and ethyl acetate added thereto, and an obtained organic layer was washed with a saturated saline solution and then dried with anhydrous magnesium sulfate. A solvent comprised therein was evaporated away under reduced pressure, and the residue was purified through silica gel chromatography and then crystallized using a mixed solvent of ethyl acetate and hexane to obtain 0.70 g of Compound (2). This is Dye (2) of the present invention.

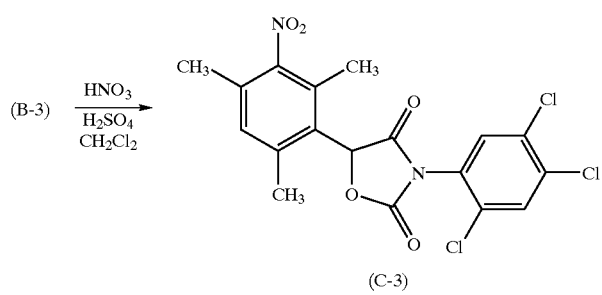

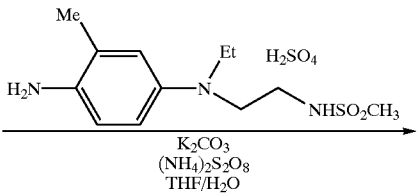

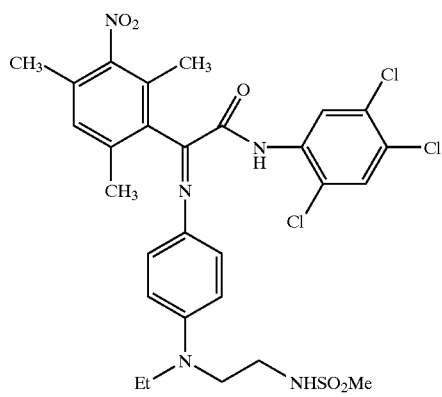

Compound (2)

Production Example 4

Production of Compound (3)

Compound (3) can be synthesized according to the reaction process shown below.

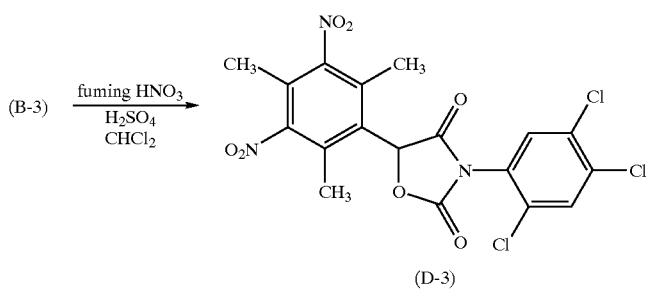

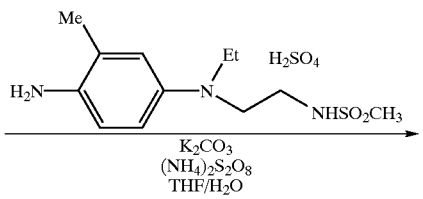

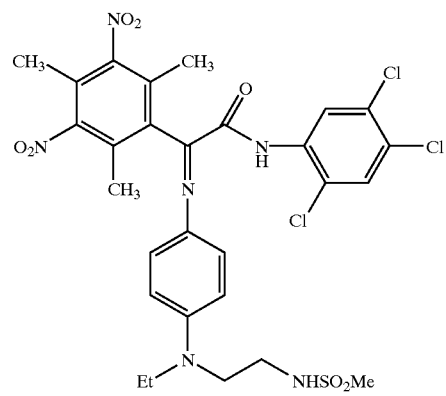

Compound (3)

4.5 ml of concentrated sulfuric acid was dropwise added to 6 ml of fuming nitric acid (specific gravity: 1.52) with the mixture was cooled with ice, and the mixture was stirred for 10 minutes. A solution of 1.3 g of Compound (B-3) dissolved in 15 ml of chloroform was dropwise added thereto it over a period of 5 minutes while the mixture was cooled with ice, and then the mixture was stirred at room temperature for 1 hour. The reaction mixture was poured into water with ice, and extracted with ethyl acetate. An obtained organic layer was washed with an aqueous solution of potassium carbonate and a saturated saline solution, and then dried with anhydrous magnesium sulfate. A solvent comprised therein was evaporated away under reduced pressure, and the residue was crystallized using a mixed solvent of ethyl acetate and hexane to obtain 0.93 g of Compound (D-3).

A solution of 2.2 g of ammonium persulfate dissolved in 15 ml of water was gradually added to a mixture of 0.57 g of Compound (D-3), 0.79 g of N-ethyl-N-(2-methanesulfonamidoethyl)-3-methyl-4-aminoaniline sulfate, 40 ml of THF and 40 ml of 1 N aqueous solution of potassium hydroxide while the mixture was stirred at 50° C. After being stirred for 10 minutes, the resulting solution was extracted with water and ethyl acetate added thereto, and an obtained organic layer was washed with diluted hydrochloric acid and a saturated saline solution and then dried with anhydrous magnesium sulfate. A solvent comprised therein was evaporated away under reduced pressure, and the residue was purified through silica gel chromatography and then crystallized using a mixed solvent of ethyl acetate and hexane to obtain 0.69 g of Compound (3) This is Dye (3) of the present invention.

Comparative Example
Preparation of Comparative Dye (CD-1)

A solution of 1.45 g of ammonium persulfate dissolved in 10 ml of water was gradually added to a mixture of 0.85 g of Coupler (C-1) mentioned below, 0.80 g of N-ethyl-N-(2-methanesulfonamidoethyl)-3-methyl-4-aminoaniline sulfate, 3.75 g of sodium carbonate, 60 ml of chloroform and 50 ml of water while the mixture was stirred at room temperature. After the resulting solution was stirred for 1 hour, an obtained chloroform layer was separated and purified through silica gel chromatography. 0.72 g of a comparative yellow azomethine dye, Comparative Dye (CD-1), was obtained.

Coupler (C-1)

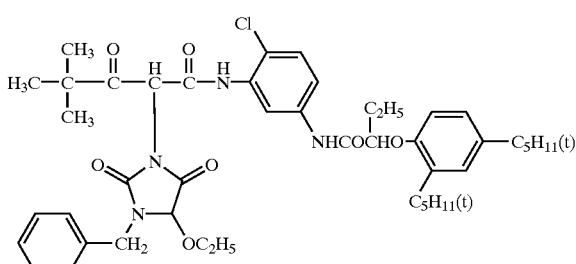

Comparative Dye (CD-1)

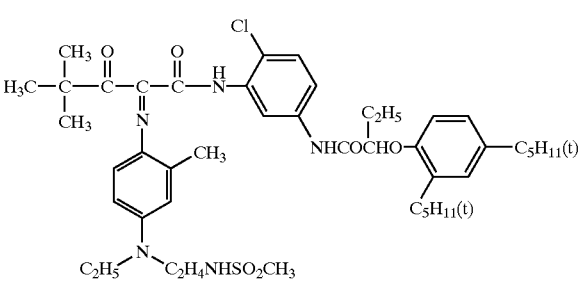

Determination of Molecular Absorption Coefficient

Molecular absorption coefficients of Comparative Dye (CD-1), obtained in the above-described comparative example, and Dyes (6), (1), (2) and (3) of thepresent invention, obtained in the examples were determined as mentioned below.

1.5 mg of each of Comparative Dye (CD-1) and Dyes (6), (1), (2) and (3) of the present invention was precisely weighed in a 100-ml messflask, and dissolved in 100 ml of ethyl acetate added thereto. In this way, sample solutions 101 (containing Comparative Dye (CD-1)), 102 (containing Dye (6)), 103 (containing Dye (1)), 104 (containing Dye (2)) and 105 (containing Dye (3)) were obtained.

Each of the sample solutions 101 to 105 was put into a quartz cell having a thickness of one centimeter. Using a UV and visible spectrophotometer (manufactured by Shimazu Corp.), a visible absorption spectrum of each sample was obtained. The molecular absorption coefficient of each sample was respectively derived therefrom. The molecular absorption coefficient at a maximum absorption wavelength of each sample is shown in Table 1 below.

TABLE 1

| Sample No. | Type of dye | Molecular absorption coefficient | |
|---|---|---|---|
| 101 | CD-1 | $1.65 \times 10^4$ | Comparative example |
| 102 | (6) | $2.11 \times 10^4$ | Example |
| 103 | (1) | $2.31 \times 10^4$ | Example |
| 104 | (2) | $2.57 \times 10^4$ | Example |
| 105 | (3) | $2.72 \times 10^4$ | Example |

From Table 1, it is understood that the molecular absorption coefficient of each of the dyes of the present invention is larger than that of the comparative dye. Acid-Fading Test of Dyes.

The Comparative Dye (CD-1) and Dyes (6), (1), (2) and (3) were evaluated for their resistance to acid, according to the method mentioned below.

1.0 mg of each of Comparative Dye (CD-1) and Dyes (6), (1), (2) and (3) of the present invention was dissolved in 15 ml of NMP (1-methyl-2-pyrrolidinone of 99% purity for peptide synthesis) to prepare sample solutions 201 (containing Comparative Dye (CD-1)), 202 (containing Dye (6)), 203 (containing Dye (1)), 204 (containing Dye (2)) and 205 (containing Dye (3)).

0.49 g of boric acid, 8 ml of 1 N aqueous solution of acetic acid and 16 ml of 1 N aqueous solution of phosphoric acid were mixed in a 200 ml messflask to prepare a Britton-Robinson buffer solution (hereinafter abbreviated to "B.R. buffer A"), and phosphoric acid was added thereto to give the buffer solution a pH of 1.15. This solution was kept at 60° C. The buffer solution was added to each of the sample solutions 201 to 205 so as to provide 25 ml of each of the resulting samples. Immediately after their preparation, and after being kept at 60° C. for 4 hours, the samples were evaluated with a UV and visible spectrophotometer (manufactured by Shimazu Corp.) to obtain a absorption spectrum of each sample. A molecular absorption coefficient at a maximum absorption wavelength of each sample was respectively derived therefrom.

The absorbance of each sample before the acid-fading test was compared with that after test, i.e. after being kept at 60° C. for 4 hours, and a color density retentiveness (%) (remaining ratio) of each sample was obtained. This indicates the resistance to acid of each dye tested. The results are given in Table 2 below.

TABLE 2

| Sample No. | Type of dye | Remaining ratio (%) | Remarks |
|---|---|---|---|
| 201 | CD-1 | 15 | Comparative example |
| 202 | (6) | 97 | Example |
| 203 | (1) | 99 | Example |
| 204 | (2) | 98 | Example |
| 205 | (3) | 96 | Example |

As shown in Table 2, it is clear that the yellow azomethine dye compounds of the present invention are all excellent in resistance to acid.

As described in detail above with reference to the preferred embodiments, the azomethine yellow dye compound of the present invention has a large absorption coefficient and it is stable against acid hydrolysis. The azomethine yellow dye compound is constituted such that it has a p-aminophenyl group bonded to the nitrogen atom in the azomethine moiety thereof, an aryl group and a carbamoyl group both bonded to the carbon atom in the azomethine moiety thereof, and a hydrogen atom bonded to the nitrogen atom in the carbamoyl group.

What is claimed is:

1. An azomethine yellow dye compound represented by the following general formula (I):

General formula (I)

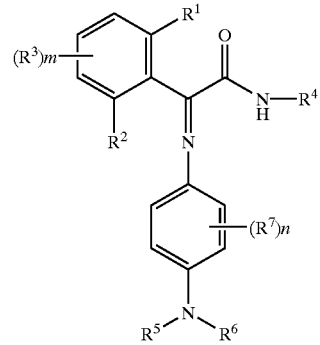

wherein, in the general formula (I), $R^1$ and $R^2$ each independently represent a hydrogen atom or a substituent; $R^3$ represents a substituent; m indicates an integer from 0 to 3; when m is 2 or greater, $R^3$'s may be the same as or different from each other, and the $R^3$'s may be bonded to each other to form a condensed ring; $R^3$ may be bonded to $R^1$ or $R^2$ to form a condensed ring; $R^4$ represents an aryl group or a heterocyclic group; $R^5$ and $R^6$ each independently represent a hydrogen atom or a substituent; $R^7$ represents a substituent; n indicates an integer from 0 to 4; and when n is 2 or greater, $R^7$'s may be the same as or different from each other, and the $R^7$'s may be bonded to each other to form a condensed ring; $R^7$ may be bonded to $R^5$ or $R^6$ to form a condensed ring; and $R^5$ and $R^6$ may be bonded to each other to form a ring.

2. The azomethine yellow dye compound according to claim 1, wherein at least one of $R^1$ and $R^2$ in general formula (I) is a substituent.

3. The azomethine yellow dye compound according to claim 1, wherein both $R^1$ and $R^2$ in general formula (I) are substituents.

4. The azomethine yellow dye compound according to claim 1, wherein $R^1$ and $R^2$ in general formula (I) each independently represent one of a halogen atom, an alkyl group and an alkoxy group.

5. The azomethine yellow dye compound according to claim 1, wherein both $R^1$ and $R^2$ in general formula (I) are methyl groups.

6. The azomethine yellow dye compound according to claim 1, wherein $R^3$ is an electron-attractive substituent having a Hammett's substituent constant $\sigma_p$ of 0 or greater.

7. The azomethine yellow dye compound according to claim 1, wherein $R^3$ is an electron-attractive substituent having a Hammett's substituent constant $\sigma_p$ from 0.1 to 1.5.

8. The azomethine yellow dye compound according to claim 1, wherein $R^3$ is an electron-attractive substituent having a Hammett's substituent constant $\sigma_p$ from 0.3 to 1.0.

9. The azomethine yellow dye compound according to claim 1, wherein $R^4$ in general formula (I) is an aryl group substituted with a halogen atom, an alkoxy group or an aryloxy group at an ortho-position relative to an anilide nitrogen to which $R^4$ is bonded.

10. The azomethine yellow dye compound according to claim 1, wherein $R^4$ in general formula (I) is one of a substituted aryl groups having from 6 to 30 carbon atoms and a unsubstituted aryl groups having from 6 to 30 carbon atoms.

11. The azomethine yellow dye compound according to claim 1, wherein $R^4$ in general formula (I) is a group selected from the group consisting of monovalent groups which are derived from aromatic or non-aromatic heterocyclic compound having 5 or 6 members heterocyclic ring by removing one hydrogen atom from the compound.

12. The azomethine yellow dye compound according to claim 1, wherein $R^4$ in general formula (I) is one of a 5-membered aromatic heterocyclic group having from 3 to 30 carbon atoms and 6-membered aromatic heterocyclic group having from 3 to 30 carbon atom.

13. The azomethine yellow dye compound according to claim 1, wherein $R^5$ and $R^6$ in general formula (I) each independently represent an alkyl group.

14. The azomethine yellow dye compound according to claim 1, wherein each of $R^5$ and $R^6$ is selected from the group consisting of a methyl group, an ethyl group, a 2-hydroxyethyl group and a 2-methanesulfonylaminoethyl group.

15. The azomethine yellow dye compound according to claim 1, wherein n in general formula (I) is 1 or 0.

16. The azomethine yellow dye compound according to claim 1, wherein $R^7$ is at least one selected from the group consisting of an alkyl group, an alkoxy group and an acylamino group.

17. The azomethine yellow dye compound according to claim 1, wherein $R^7$ is a methyl group provided at an ortho-position relative to the azomethine nitrogen in the compound.

\* \* \* \* \*